United States Patent [19]

Hudson

[11] Patent Number: 4,601,702
[45] Date of Patent: Jul. 22, 1986

[54] VOLUMETRIC INFUSION ACTUATOR

[75] Inventor: James E. Hudson, Dallas, Tex.

[73] Assignee: Quest Medical, Inc., Carrollton, Tex.

[21] Appl. No.: 612,384

[22] Filed: May 21, 1984

[51] Int. Cl.⁴ ............................................. A61M 5/00
[52] U.S. Cl. ........................... 604/246; 128/DIG. 12; 128/DIG. 13; 604/890; 604/30; 604/250
[58] Field of Search ................... 604/246, 67, 31, 151, 604/153, 890–893, 250, 30; 128/DIG. 12, DIG. 13

[56] References Cited

U.S. PATENT DOCUMENTS

| | | | |
|---|---|---|---|
| 3,994,294 | 11/1976 | Knute | 128/DIG. 12 |
| 4,037,598 | 7/1977 | Georgi | 128/214 E |
| 4,126,132 | 11/1978 | Portner et al. | 128/DIG. 12 |
| 4,191,184 | 3/1980 | Carlisle | 128/214 F |
| 4,204,538 | 5/1980 | Cannon | 128/214 R |
| 4,207,871 | 6/1980 | Jenkins | 128/214 R |
| 4,217,993 | 8/1980 | Jess et al. | 604/246 |
| 4,230,244 | 10/1980 | Zissimopoulos | 604/246 |
| 4,261,356 | 4/1981 | Turner et al. | 604/246 |
| 4,315,523 | 2/1982 | Mahawili | 137/486 |
| 4,391,598 | 7/1983 | Thompson | 604/65 |
| 4,431,425 | 2/1984 | Thompson et al. | 604/246 |
| 4,493,709 | 1/1985 | Smith | 604/246 |

FOREIGN PATENT DOCUMENTS

| | | | |
|---|---|---|---|
| 1807979 | 7/1969 | Fed. Rep. of Germany | 604/153 |
| 1368566 | 10/1974 | United Kingdom . | |
| 2043594 | 2/1980 | United Kingdom . | |
| 2053378 | 2/1981 | United Kingdom | 128/DIG. 12 |

*Primary Examiner*—Stephen C. Pellegrino
*Assistant Examiner*—Mark Rooney
*Attorney, Agent, or Firm*—Roger Clapp

[57] ABSTRACT

A volumetric infusion actuator providing a slot means for receiving a valved cassette having exposed valve pads. An actuation means for automatically moving individual arms into and out of engagement with the valve pads according to a predetermined cycle which governs flow through the cassette.

1 Claim, 11 Drawing Figures

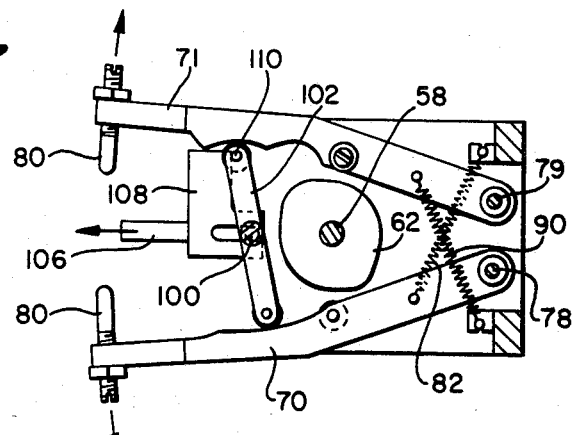
FIG. 7
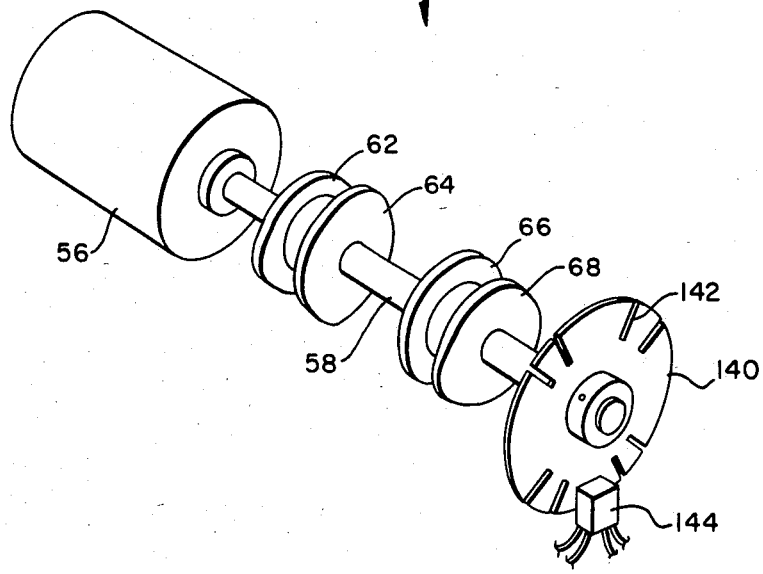
FIG. 8
FIG. 11A   FIG. 11B   FIG. 11C   FIG. 11D

VOLUMETRIC INFUSION ACTUATOR

TECHNICAL FIELD

This invention relates to the volumetric infusion of fluids into patients, and more particularly to methods and apparatus for accomplishing such infusions utilizing a metering chamber divided into two compartments by a movable membrane.

BACKGROUND ART

In the field of therapeutic fluid delivery, various approaches to instrumentation for controlling the infusion rate have been proposed. Some of the instrumentation previously disclosed utilizes a metering chamber divided into two compartments by a movable membrane. For example, U.S. patent application Ser. No. 404,811, filed Aug. 3, 1982, and owned by the owner of the present application, describes in detail a number of such systems for achieving volumetric accuracy of delivery. That application discloses a disposable cassette containing a dual chamber, with each compartment of the chamber being provided with a valved inlet and outlet. Upon opening of a valve pair comprising an inlet and an outlet on opposite sides of the membrane separating the two compartments, exactly one chamber's volume of fluid is delivered to the patient, and then fluid flow stops. The alternation of opening and closing of the two pairs of valves thus provides a digitized flow of fluid in precise volumetric quantities. By selecting the rate at which the valve states are initiated, the user may provide for the precise desired overall volumetric flow rate.

As can be seen from that application, the disposable cassette which carries the metering chamber and the four valves associated with the chamber must cooperate with an actuator for effecting the valve movement. Such an actuator, several examples of which are given in the application, serves as the mechanical interface between the microprocessor or other control intelligence which generates the timed control signals to achieve the desired volumetric flow rate, and the valves of the disposable cassette which actually serve to gate the fluid flow through the cassette. The invention of this application is directed to improvements in such mechanical interfaces.

Patent art of interest in the general field of fluid flow control utilizing chambers having a movable membrane may be found in U.S. Pat. Nos. 4,204,538, 4,207,871, 4,121,584, and in U.K. patent application Ser. No. 2,043,594 (published Oct. 8, 1980).

SUMMARY OF THE INVENTION

In accordance with this invention, a fluid delivery cassette actuator is provided for receiving a disposable cassette having a plurality of externally accessible valves. The actuator includes stationary slot means for receiving the valved cassette, valve actuator arms adjacent the sides of the slot means and corresponding to each one of the valves on the cassette, so as to be movable into engagement with the cassette valves when the cassette is located in its operating position in the slot means. Biasing means are provided which normally force all of the arms into engagement with the cassette valves in order to close them. Separate control means for each valve actuator move the actuator toward and away from the slot means to close and open each valve separately.

In a further aspect of the invention, eject means are provided which are operable by the user to overcome the biasing means for the valve actuator arms and move all arms back from the cassette. The eject means also operates an ejection pin to push the cassette from its operating position in the slot following retraction of the actuator arms.

In a specific embodiment, the eject means comprises a button which may be depressed to rotate a shaft carrying a spreader bar to force all of the actuator arms away from the cassette and then to move the ejection pin outwardly in the slot.

In a further aspect of the invention, the eject means cooperates with an insertion setup means which is automatically responsive to the insertion of the cassette into the slot means to overcome the eject means and permit the biasing means to cause the actuator arms to engage the cassette valves.

The control means for the actuator arms may consist of a cam corresponding to each actuator arm driven by a single motor shaft so that the degree of rotation of each cam determines whether its corresponding arm is in an open or closed position.

BRIEF DESCRIPTION OF THE DRAWINGS

A more complete understanding of the invention and its advantages will be apparent from the following description when taken in conjunction with the accompanying drawings, in which:

FIG. 7 is a simplified cross sectional view taken along the line 7—7 in FIG. 5;

FIG. 8 is perspective illustration of the shaft sensor disc and four cams for control of movement of the actuator's arm;

FIGS. 11A-D illustrate displays to be given to the user to indicate the relative availability of pressure to deliver flow at the requested rate.

DETAILED DESCRIPTION OF THE DRAWINGS

Figure 1:
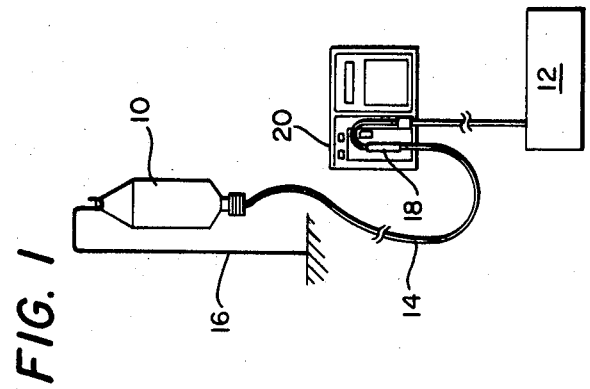
FIG. 1 illustrates a fluid delivery system incorporating a device constructed in accordance with the present invention.
Figure 4A:
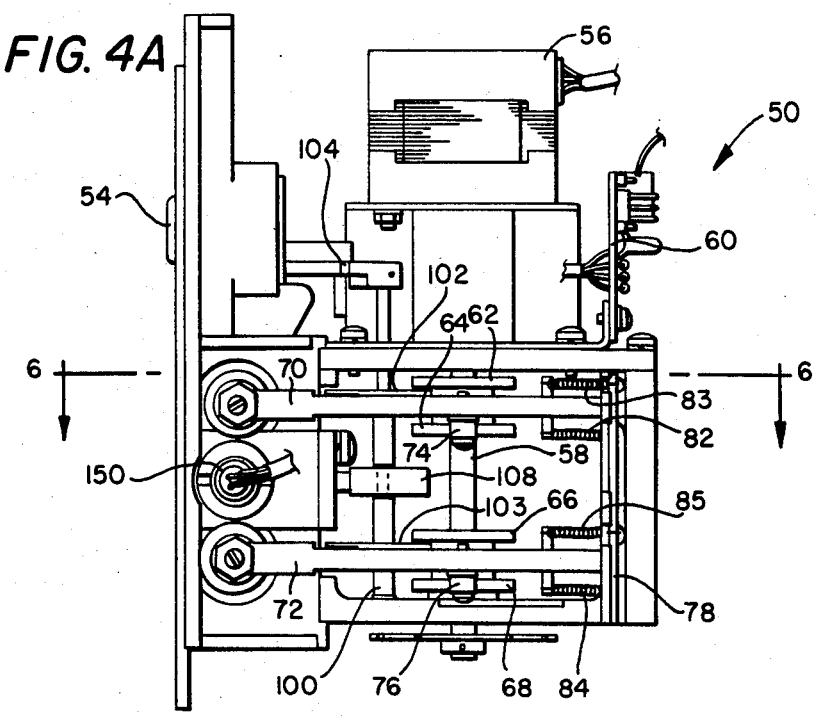
FIG. 4A is a right side view illustrating the mechanical actuator of FIG. 3, in the operating position.
Figure 4B:
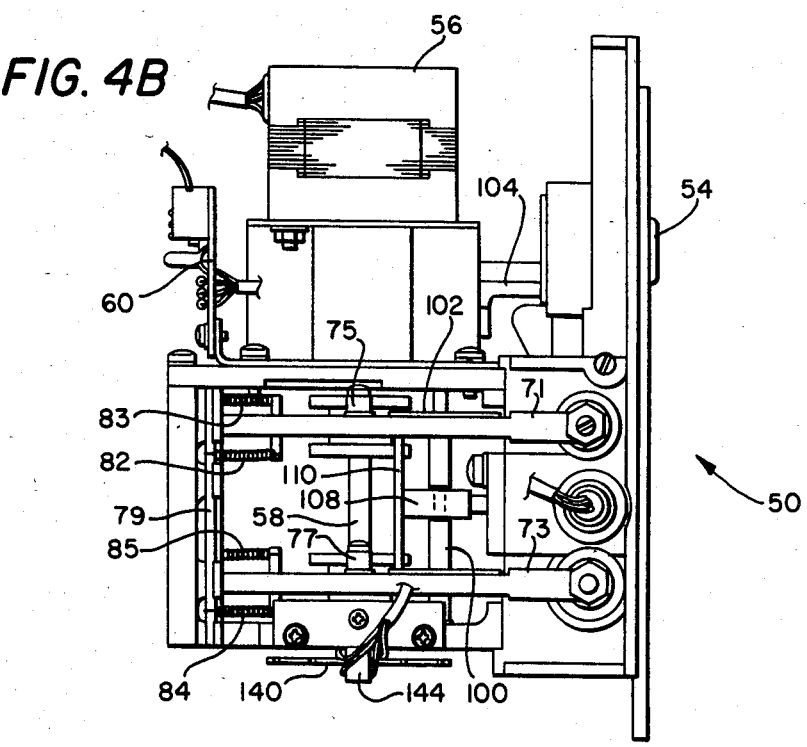
FIG. 4B is a left side view similar to FIG. 4A.

In accordance with this invention, as illustrated in FIG. 1, fluid may be delivered intravenously from fluid container 10 to a patient 12 through delivery tubing 14. Container 10 is suspended above the patient 12 by hanging it on a pole 16. Delivery tubing 14 is a disposable administration set which incorporates a volumetric metering cassette 18 which is inserted in electronic flow control instrument 20 for operation.

Figure 2:
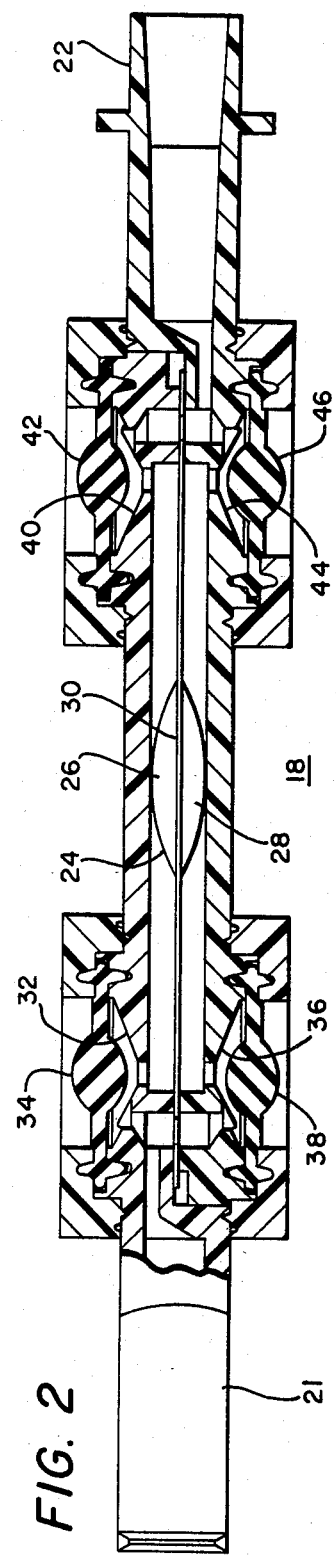
FIG. 2 illustrates a disposable cassette preferred for use in conjunction with the actuator of this invention in a fluid delivery system such as depicted in FIG. 1.

Cassette 18 is illustrated in cross section in FIG. 2. A detailed description of the various parts of cassette 18 is set forth in co-pending U.S. patent application Ser. No. 404,811, filed Aug. 3, 1982, which is hereby incorporated by reference in full. Cassette 18 has an entrance nipple 21 and exit nipple 22 located at opposite ends of the cassette.

A precisely formed volumetric metering chamber 24 is located in the central area of cassette 18 and is divided into compartments 26 and 28 by a flexible membrane 30. Entrance 21 communicates with compartment 26 through valve seat 32 which is provided with a valve 34 movable between opened closed positions. Entrance 21 communicates with compartment 28 through valve seat 36 having a valve 38 movable between open and closed positions.

Compartment 26 has fluid communication with the exit 22 of cassette 18 through valve seat 40 which is provided with valve 42 movable between open and closed positions. Compartment 28 communicates with cassette exit 22 by way of valve seat 44 which is provided with valve 46 movable between open and closed positions. In FIG. 2, all four valves 34, 38, 42, and 46 are shown in their open position which they would assume when outside instrument 20. Each of these valves is externally accessible so as to be movable into engagement with its corresponding valve seat to close the same.

Figure 3:
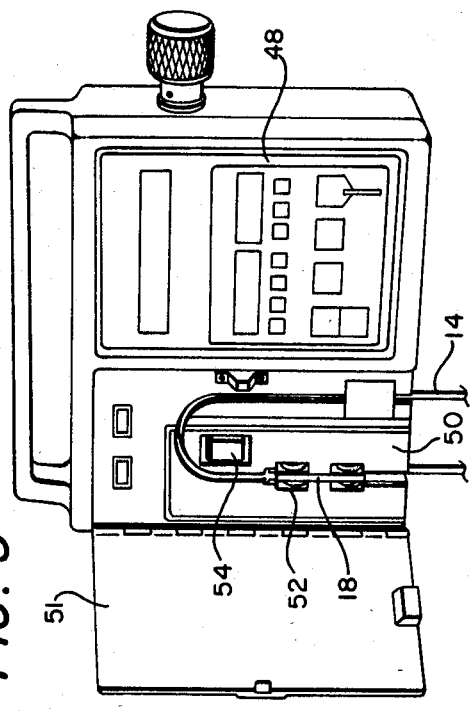
FIG. 3 is a front prospective view of the system forming the preferred embodiment of this invention.

The delivery tubing 14 with cassette 18 are shown located for operation in instrument 20 in FIG. 3. Instrument 20 is provided with various informational displays and operator controls on its right face 48. Mechanical actuator 50 is located in the left half of instrument 20 behind door 51. Actuator 50 is provided with a stationary slot 52 shaped to receive cassette 18 edgewise. An eject button 54 is mounted on actuator for use by the operator in moving cassette 18 from the stationary slot 52 when removal is desired.

As illustrated in FIGS. 4–8, actuator 50 is provided with a stepper motor 56 which drives valve actuator control shaft 58 in response to the command signals of electronic circuitry mounted on circuit board 60. Cams 62, 64, 66, and 68 are mounted in spaced positions on shaft 58 and provide control for the opening and closing of valve buttons 42, 46, 34, and 38, respectively. Each of said valves has a corresponding actuator arm mounted for engagement with the valve under the control of the corresponding cam. On one side of slot 52, actuator arm 70 is positioned to open and close valve 46, and actuator arm 72 controls opening and closing of valve 38. On the opposite side of slot 52, activator arm 71 is operable to open and close valve 42, and actuator arm 73 is operable to open and close valve 34. Arms 70 and 72 are pivoted about shaft 78 at one end. Arms 71 and 73 are pivoted about shaft 79 at one end. At the opposite end, each arm carries an actuator plunger 80 for engaging its corresponding valve. Arms 70, 71, 72, and 73 are biased to the valve-engaging position by springs 82, 83, 84, and 85, respectively.

Each of the arms 70–73 is positioned for engagement with a valve and operates under the control of a corresponding cam. Arms 70, 71, 72, and 73 are moved between valve-open and valve-close positions by cams 64, 62, 68, and 66, respectively. The arms 70, 71, 72, and 73 carry, respectively, cam follower rollers 74, 75, 76, and 77 for engaging the corresponding cams to product the arm movements.

Actuator 50 carries a rotatable vertical spreader shaft 100 formed with a pair of vertically spaced spreader bars 102 and 103. The upper spreader bar 102 is positioned adjacent arms 70 and 71, and the lower spreader bar 103 is adjacent arms 72 and 73. Eject button 54 and shaft 100 are provided with linkage 104. Linkage 104 includes linear translation bar 104a which is pinned near its back end to rotator bar 104b carried by shaft 100. Upon depression of button 54, bar 104a moves to the rear moving its pin connection with rotator 104b rearward. This causes shaft 100 to move counter-clockwise (when viewed from above), and this causes spreader bars 102 and 103 to rotate with shaft 100 to push arms 70–73 back into retracted positions, as shown in FIG. 7. In the rear of cassette slot 52 is a slidable cassette ejection pin 106 mounted on ejection pin block 108. Ejection pin 106 is movable between an operational position flush with the rear of slot 52, and an eject position extending forwardly into slot 52. A vertical bar 110 connects spreader bars 102 and 103 adjacent block 108.

Figure 6:
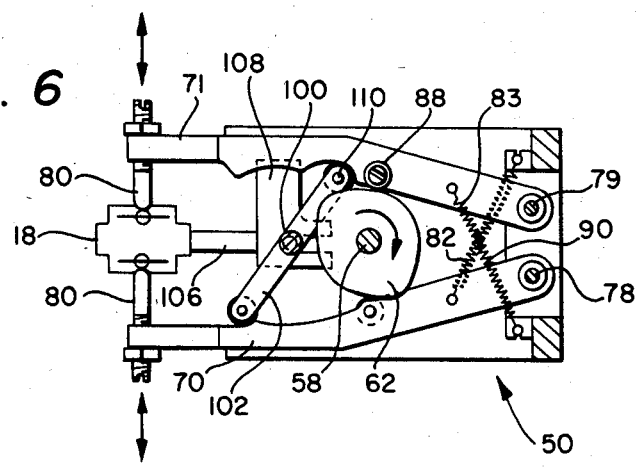
FIG. 6 is a simplified sectional view taken along the line 6—6 in FIG. 4.

In FIG. 7, the state of the actuator is shown prior to insertion of cassette 18. The spreader bar 102 has been rotated counter-clockwise by depression of eject button 54 to spread the four arms 70–73 apart from their cassette engaging positions, and bar 110 has caused block 108 and thus cassette ejection pin 106 to be moved forwardly so that pin 106 extends into the slot 52 from the rear. In this condition, the slot 52 is opened for receipt of cassette 18, as the valve actuator plungers 80 are away from the slot. When a cassette is inserted into the slot 52 as illustrated in FIG. 6, the mechanical engagement of the cassette 18 against ejection pin 106 in the rear of slot 52 causes the pin to move rearwardly forcing block 108 back against bar 110 to rotate spreader shaft 100 in the clockwise direction, and the spring bias of the actuator arms 70–73 forces the arms into engagement with the valves on cassette 18, as illustrated in FIG. 6.

Figure 5:
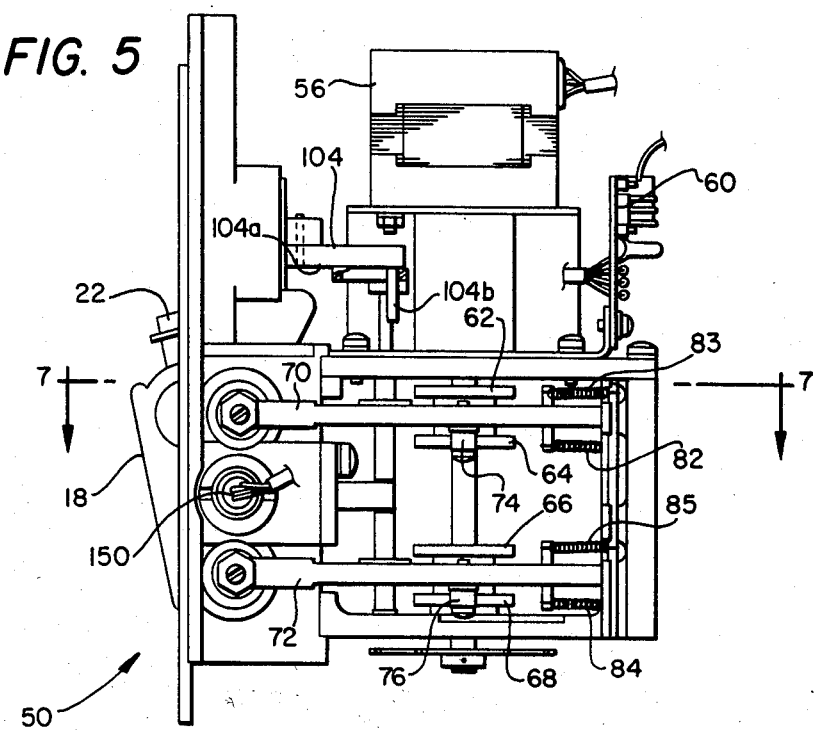
FIG. 5 is a view similar to FIG. 4A, except that the actuator is in the cassette-ejected position.

When eject button 54 is depressed, its depression operates through linkage 104 to cause spreader shaft 100 to rotate in the counter-clockwise direction, spreading the arms apart, and then causing bar 110 to engage block 108 moving cassette ejection pin 106 forward to push the cassette from the slot 52 as illustrated in FIG. 5.

Motor actuator shaft 58 also carries a slotted sensor plate 140 provided with radially extending peripheral slots 142 based about its periphery. An optical sensor 144 is mounted adjacent slots 142 for producing signals to stop the operation of motor 56 at eight spaced locations of rotation of the shaft. Slots 142 are situated in pairs defining an identical short arc between each member of the pair, and a longer arc between adjacent pairs. The short arc between members of a slot pair is approximately 30 degrees, while the arc between the closest slot of adjacent slot pairs is 60 degrees.

A pair of optical sensors 150 are located on opposite sides of slot 52 directly adjacent the location in which the center of metering chamber 24 is positioned. The sensors provide indications of movement of membrane 30 by comparison of reflected light signals from the membrane at different times in the cycle of the apparatus. Such an optical sensor is disclosed in detail in U.S. Pat. No. 4,431,425, incorporated herein by reference. A pair of optical signal sensors is used in parallel, one on each side, to enhance the reliability of the sensor signals, particularly when opaque fluids are being delivered.

Figure 9:
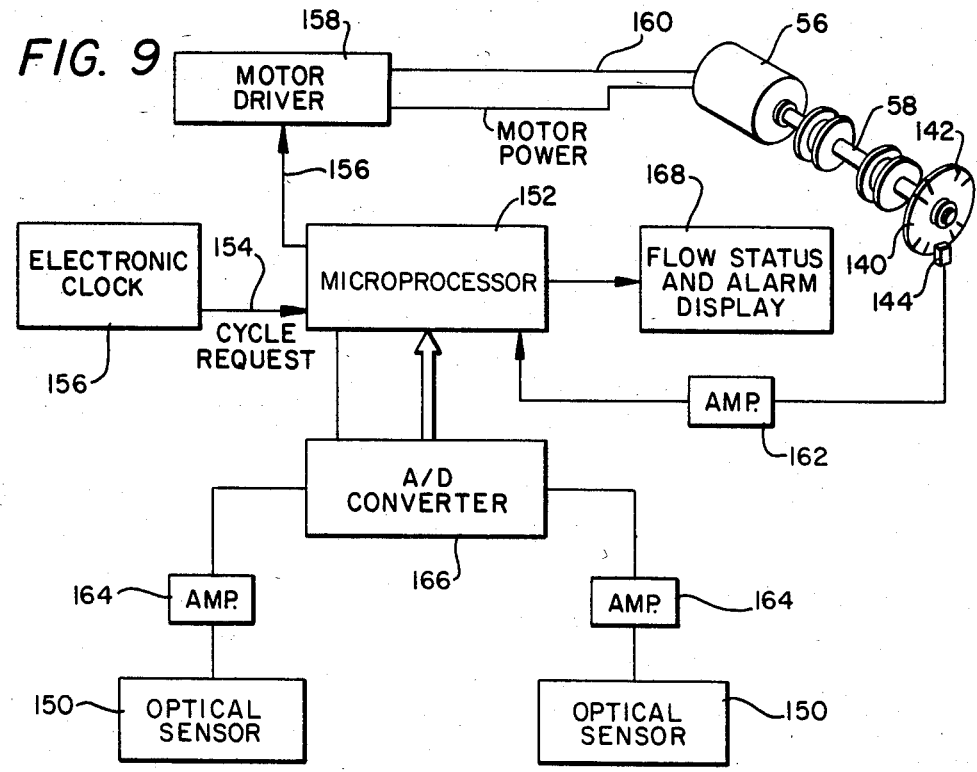
FIG. 9 is a schematic illustration of a control system for the device.

As illustrated in FIG. 9, the apparatus is operated under the control of a microprocessor 152. Timed cycle requests 154 are generated to microprocessor 152 by means of electronic clock 156. The timing of the cycle request depends directly upon the average rate of volumetric delivery requested by the user. If, for example, the chamber is 0.1 milliliter in volume and the user requests an average delivery rate of 6 milliliters per hour, then the cycle requests will be one minute apart. Thus, 60 chambers of fluid will be delivered each hour. Microprocessor 152 provides signals through line 160 to the motor driver 158, which provides motor power on lines 160 to motor 56 to turn shaft 58. Signals from optical sensor 144 sensing the presence of one of the slots 142 on sensor plate 140 are provided to microprocessor via amplifier 162 to stop the motor. The signals on detection of membrane movement from the optical sensors 150 are provided by way of amplifiers 164 through A/D converter 166 to microprocessor 152. Microprocessor 152 generates signals to provide flow status and alarm display information 168.

Figure 10:
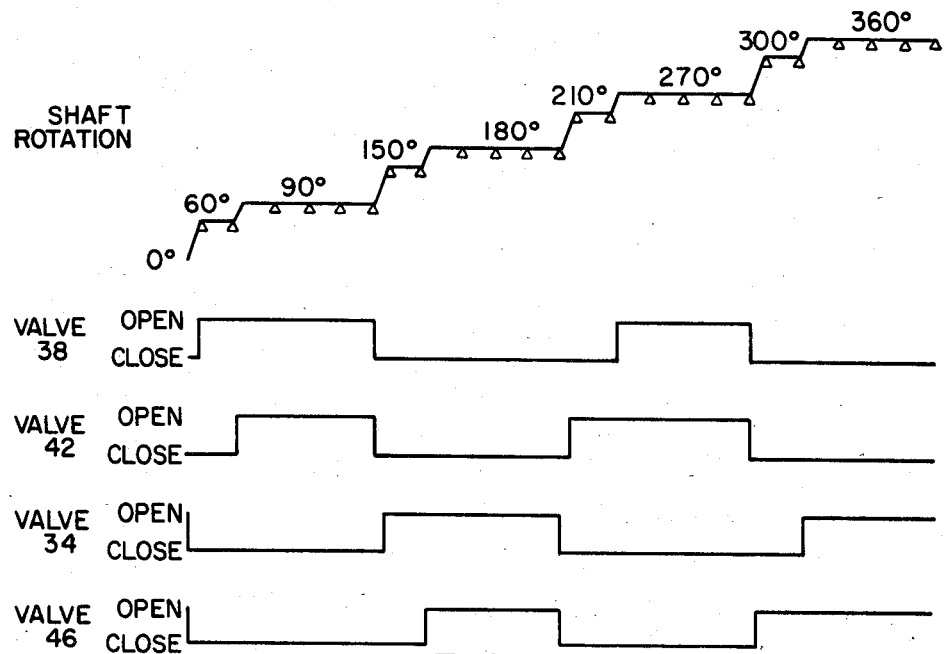
FIG. 10 is a time graph illustrating the sequence of movement of shaft and valves through a cycle of the actuator.

The timing of the valve movements between open and closed positions for valves 34, 38, 42, and 46 is illustrated in FIG. 10 for one complete rotation of the motor shaft 58. Prior to each delivery of an increment of fluid contained in chamber 24, a cycle request is generated by clock 156. Four of such cycle requests cause movement of the motor shaft 58 through a complete 360 degree rotation. Upon a cycle request, the shaft is first rotated through an arc of 60 degrees and held for a brief period. Then the shaft is rotated through an additional 30 degrees, and held for the major part of the period between cycle requests, constituting approximately 80 percent of the cycle time. During this period, a pair of diagonally opposed valves are open to permit the delivery of one fluid increment. Prior to the beginning of the first cycle request illustrated in FIG. 10, valves 34 and 46 have been opened, while valves 38 and 42 are closed. As the shaft 58 rotates toward its first stop, all valves are initially closed, and then, the single valve 38 is opened when the shaft arrives at the 60 degree rotation point. After a brief pause, the shaft rotates an additional 30 degrees to also open valve 42. The valves remain in this condition for the remainder of the time until the next clock cycle request is generated. The movement of valves upon each subsequent cycle request is similar to the one described, except that the open valve pairs are alternated and the single valve opened alone for the brief period is a different one of the four valves during the four cycles in a single rotation of the shaft. The sampling of the membrane sensors is illustrated for the complete rotation of the shaft by the arrows in FIG. 10.

By alternately opening diagonally opposed pairs of valves upon each cycle request, the flow of one chamber full of fluid to the patient should occur through tubing 14, if gravity pressure vis-a-vis flow resistance is sufficient for delivery. At the onset of the time illustrated in FIG. 10, with valves 34 and 46 open, compartment 26 will be full of fluid, and the membrane 30 will be completely positioned against the right side of chamber 24, giving compartment 28 a zero volume. No fluid should be flowing, as the outlet from the full compartment is closed by valve 42. The cams, as the motor initially moves the shaft from the zero degree position, first move all valves to the closed position. When the shaft arrives at the 60 degree rotation position, valve 38 is open. In this position, the apparatus is held for a brief time approximately equal to 20 percent of the allotted time between cycle requests as dictated by the volumetric infusion rate desired by the user. During this period, no fluid should flow. The pause at this position is for the purpose of determining if in fact fluid is flowing by sampling the membrane sensors twice during the period. If the membrane sensors indicate membrane movement, this would be indicative of a leak at one of the valves which are supposed to be closed. Such a leak might be caused, for example, by a broken arm which fails to engage a valve to close it. Accordingly, if movement of the membrane is detected during this brief pause period, an alarm signal is generated to advise the user of the problem.

If the leak pause is successfully completed, no valve membrane movement being shown, the shaft moves to the 90 degree position to also open valve 42. In this position, the head pressure of fluid through valve 38 causes the fluid to flow into compartment 28, emptying compartment 26 and delivering exactly 0.1 milliliter of fluid through open valve 42. When emptying is complete, flow will stop, and the apparatus will remain in this condition with an empty compartment 26 and a full compartment 28, and no fluid flow. During the period when valves 38 and 42 are open, the membrane sensors are sampled four times in order to ascertain the discrete period within which the fluid flow is completed. These samplings occur at roughly each quarter point during the time which valves 38 and 42 are open.

U.S. Pat. No. 4,431,425 describes a single pair of samplings to ascertain that the membrane has in fact moved in response to valve openings so that an alarm can be generated in the event that the membrane has not moved in response to valve control. Such an alarm could be caused by an occlusion in the line, or other failure of the system to have sufficient gravity head pressure to deliver the desired increment of fluid in the time available given the flow resistance provided by the patient and the tubing. As illustrated in FIG. 10, the additional sampling of the membrane gives the capability of providing more information to the user with respect to the comparison between available head pressure and the flow resistance in the system.

Displays are illustrated in FIG. 11, for providing such information to the user in accordance with the data obtained by the four samplings of the membrane sensors during each time a pair of valves is open.

If the sensors indicate that membrane movement was completed during the first quarter of the time available, a display of a single bar such as shown in FIG. 11-A is made, advising the user that the available pressure is more than adequate to deliver fluid at the requested rate given the flow resistance being encountered. When the sensors indicate that movement was completed during the second quarter of the available time period, two bars are displayed as illustrated in FIG. 11-B. This indicates that pressure is still adequate to deliver fluid at the requested rate, but at a lesser level than with the signal of FIG. 11-A. The display of three bars as shown in FIG. 11-C, indicates that the membrane sensor sampling shows completion of membrane movement during the third quarter of the available time period. This indicates that the major portion of the available time is being used for movement, which may indicate a problem in occlusion, flow resistance, or other heightening of back pressure potentially preventing delivery, although the fluid delivery was complete.

Finally if the membrane sensor sampling indicates that the membrane was still moving during the fourth quadrant of the available time, a star is generated to alert the user that the existing gravity head may not be sufficient to sustain flow at the requested rate, and that an alarm condition may occur.

At flow rates selected by the user which require times between successive cycle requests of 45 seconds or less, the breakdown of the cycle is substantially as described above, with roughly 20 percent of the time between cycle requests being utilized for the leak pause period when only one valve is open, and the remainder of the time being available for flow on the opening of a pair of valves. At lower rates, the leak pause is maintained at approximately 9 seconds, and the sampling of four quarters for determining the pressure availability signals illustrated in FIG. 11 is limited to 36 seconds, so that each quarter's sampling occurs approximately 9 seconds apart.

As can be seen, each four successive cycle requests results in a one complete rotation of shaft 58. After each cycle request, one of the valves is opened for a brief pause period to detect leaks for alarm purposes. Following the leak pause period, after each one of the four cycle requests, a valve pair opens to a volume of fluid equal to the volume of the cassette chamber, provided that the gravity head is sufficient vis-a-vis flow resistance, to cause delivery. The detection of completion of membrane movement during any of the four quarters of time in which a pair of valves is open for flow permits the giving of the information concerning the adequacy of pressure to deliver flow at the requested rates, as indicated by the displays of FIG. 11.

Although only one embodiment of a method and apparatus for volumetric infusion actuator in accordance with the present invention has been illustrated in the accompanied drawing and described in the foregoing detailed description, it will be understood that the invention is not limited to the embodiments disclosed, but is capable of numerous rearrangements, modifications, and substitutions of parts and elements without departing from the scope and spirit of the invention.

I claim:

1. A fluid delivery cassette actuator for a valved cassette comprising:
   (a) slot means for receiving a valved cassette having exposed valve pads;
   (b) valve actuator arms movable into engagement with the valve pads of a cassette located in operating position in the slot means and actuation means for automatically moving each individual arm independently into and out of engagement with its valve pad in accordance with a predetermined cycle;
   (c) biasing means normally forcing all of the arms into engagement with the valve pads to close them;
   (d) eject means operable to overcome biasing means and move all arms back from the cassette, and then to push the cassette from the operating position in the slot; and
   (e) insertion setup means responsive to insertion of a cassette into the operating position in the slot to automatically disable the eject means and permit the biasing means to cause the arms to engage the valve pads.

* * * * *